United States Patent
Besemer et al.

(10) Patent No.: US 8,129,581 B1
(45) Date of Patent: Mar. 6, 2012

(54) HYGIENIC ABSORBENT WITH ODOUR CONTROL

(75) Inventors: Arie Cornelis Besemer, Amerongen (NL); Anne-Mieke Yvonne Wilhelmina Verwilligen, Zeist (NL); Jeffrey Thornton, Huizen (NL)

(73) Assignee: SCA Hygiene Products Zeist B.V., AJ Zeist (NL)

( * ) Notice: Subject to any disclaimer, the term of this patent is extended or adjusted under 35 U.S.C. 154(b) by 0 days.

(21) Appl. No.: 09/937,326

(22) PCT Filed: Apr. 6, 2000

(86) PCT No.: PCT/NL00/00228
§ 371 (c)(1),
(2), (4) Date: Sep. 25, 2001

(87) PCT Pub. No.: WO00/59556
PCT Pub. Date: Oct. 12, 2000

(30) Foreign Application Priority Data

Apr. 6, 1999 (EP) .................................. 99201087

(51) Int. Cl.
*A61F 13/15* (2006.01)
(52) U.S. Cl. ........................................ 604/359; 604/360
(58) Field of Classification Search .................. 604/368, 604/359–360
See application file for complete search history.

(56) References Cited

U.S. PATENT DOCUMENTS

| | | | |
|---|---|---|---|
| 4,145,518 A * | 3/1979 | Morie et al. ................... | 528/272 |
| 4,685,909 A | 8/1987 | Berg et al. | |
| 5,045,322 A * | 9/1991 | Blank et al. ................... | 424/486 |
| 5,340,853 A | 8/1994 | Chmelir et al. | |
| 5,419,955 A | 5/1995 | Ehrhardt et al. | |
| 5,437,418 A * | 8/1995 | Graef et al. ...................... | 241/65 |
| 5,498,650 A * | 3/1996 | Flexman et al. ............... | 524/114 |
| 5,677,058 A * | 10/1997 | Neal et al. ...................... | 428/375 |
| 5,693,411 A | 12/1997 | Hansen et al. | |
| 5,736,595 A | 4/1998 | Günther et al. | |
| 5,801,116 A * | 9/1998 | Cottrell et al. ................. | 502/404 |
| 5,837,627 A * | 11/1998 | Halabisky et al. ............. | 442/385 |
| 6,229,046 B1 * | 5/2001 | Eyal et al. ...................... | 562/589 |
| 6,231,721 B1 * | 5/2001 | Quick et al. ................. | 162/164.1 |
| 6,521,087 B2 * | 2/2003 | Hansen et al. ................. | 162/173 |
| 6,534,572 B1 * | 3/2003 | Ahmed et al. ................. | 524/275 |

* cited by examiner

*Primary Examiner* — Lynne Anderson
(74) *Attorney, Agent, or Firm* — Buchanan Ingersoll Rooney PC

(57) ABSTRACT

A superabsorbent material with enhanced odour control and control of bacterial growth comprises a non-acidic, alkali-neutralizing compound selected from acid anhydrides, lactides, lactones and hydrolysable esters, especially cyclic acid anhydrides, lactides and lactones of γ- or δ-carboxylic acids. The superabsorbent material can be used in hygiene products such as diapers.

10 Claims, No Drawings

HYGIENIC ABSORBENT WITH ODOUR CONTROL

The present invention relates to a superabsorbent material for use in hygienic absorbent products such as diapers, sanitary napkins and the like, which has enhanced odour control and prevents bacterial growth and to a method of producing such material.

Superabsorbent materials of various types are known in the art. Examples are crosslinked polyacrylates and polysaccharides grafted with polyacrylates. A problem related to the use of superabsorbent materials is the odour caused by urine components, which cause superabsorbent materials to become objectionable long before there maximum absorbing capacity has been used. As the malodorous compounds are often alkaline materials such as amines, it has been proposed to improve odour control by adding acids to the superabsorbent material. However, the use of acids has disadvantages in that acids will lead to skin irritation.

U.S. Pat. No. 4,685,909 discloses disposable diapers and the like containing polymeric acidic pH control agents such as cellulose phosphate and polyacrylic acid.

It has been found that a superabsorbent material with improved odour control can be produced by incorporating in or combining with the superabsorbent material a non-acidic, alkali-neutralising compound selected from acid anhydrides, lactides, lactones and hydrolysable esters.

Lactides include cyclic esters of hydroxy acids, especially α-hydroxy acids such as glycolic acid and lactic acid (2,5-dioxo-1,4-dioxanes). Lactones include cyclic esters of hydroxy acids, especially γ- or δ-hydroxy acids such as butyrolactone, valerolactone, gluconolactone, glucuronolactone and corresponding lactones of other sugar acids. Examples of hydrolysable esters are cellulose acetate and starch acetate. The non-acidic compound can be chemically bound to the superabsorbent material in the form of esters such as acetylated cellulose. Anhydrides are also suitable, although they are somewhat less preferred than lactides, lactones and hydrolysable esters, possibly because their susceptibility to hydrolysis is too high. They include anhydrides of carboxylic acids, especially cyclic anhydrides of dicarboxylic or polycarboxylic acids such as succinic, glutaric, maleic, citraconic, phthalic acid.

The amount of neutralising agent (e.g. lactide and lactone) to be incorporated in or to be combined with the superabsorbent material can be 1-20% by weight, preferably 3-12% by weight with respect to the weight of the superabsorbing polymer. The amount of neutralising agent can also be expressed in molar equivalents. In particular the amount is 0.05-1 mmol, in particular 0.15-0.6 mmol per g of superabsorbing polymer.

An agent facilitating hydrolysis may be added to the neutralising agent. A suitable example is a hydrolysing enzyme, such as a lipase.

The superabsorbent materials according to the invention can be used for absorbing fluids, especially body fluids that may produce alkaline odorous components such as urine. The materials may be incorporated in any absorbent article such as sanitary napkins, incontinence pads and baby diapers. As a model for human urine, so-called synthetic urine (SU) is used to study the effectiveness of the superabsorbent materials. The composition of SU is given in table 1 below:

TABLE 1

| component | g/l | mmol/l |
|---|---|---|
| magnesium sulphate | 0.42 | 3.5 |
| potassium chloride | 4.50 | 60 |
| sodium chloride | 7.60 | 130 |
| urea | 18.00 | 300 |
| calcium sulphate dihydrate | 0.34 | 2 |
| potassium dihydrogen phosphate | 3.54 | 26 |
| disodium hydrogen phosphate | 0.745 | 5.3 |
| Triton X-100, 0.1% | 1.00 | |
| pH 5.9-6.0 | | |

EXAMPLE 1

Baby Diaper

In a baby diaper containing 13 g of polyacrylic acid as absorbent (Libero Maxi Girl), four different alkali-neutralising substances were placed under a non-woven of the diaper and on top of the pulp. 250 ml of SU was added to the diaper. After the addition, the pH was measured at six different places on the non-woven using a contact electrode, and the values were averaged. The results are summarised in table 2. It can be seen from the table that despite the high buffering capacity of the diaper (>75% of the polyacrylic acid being in the sodium salt form), the pH is lowered due to hydrolysis of the acid precursor.

TABLE 2

| neutralising substance | amount (mg) | amount (mmol) | pH after 1 h | pH after 2 h | pH after 5 h |
|---|---|---|---|---|---|
| none | — | — | 5.75 | 5.81 | 5.92 |
| lactide | 577 | 4.0 | 5.84 | 5.80 | 5.47 |
| δ-gluconolactone | 1430 | 8.0 | 5.96 | 5.85 | 5.33 |
| maleic anhydride | 600 | 6.1 | 5.70 | n.d. | 5.43 |

EXAMPLE 2

Sanitary Napkin

In a sanitary napkin (Libresse) containing CTMP (chemically treated mechanical pulp) as absorbent, three different alkali-neutralising substances were placed in the middle of the CTMP of the napkin. 15 ml of SU was added to the napkin. After the addition of the urine, the pH was measured as six different places on the non-woven using a contact electrode, and the values were averaged. The results are summarised in the following table 3. The table shows that addition of lactide lowers the pH quickly, whereas the same amount of (maleic) anhydride results in a slower but continuing pH decrease. A direct acid (citric acid) tend to be too acidic.

TABLE 3

| neutralising substance | amount (mg) | amount (mmol) | pH after 2 h | pH after 5 h |
|---|---|---|---|---|
| none | — | — | 5.76 | 5.67 |
| lactide | 34 | 0.23 | 4.51 | 4.56 |
| maleic anhydride | 23 | 0.23 | 5.36 | 4.32 |
| citric acid | 49 | 0.23 | 3.98 | 3.80 |

EXAMPLE 3

Baby Diaper 250 ml SURM was added to a baby diaper (*Libero maxi*). Different amounts of glycolide, from 0.2 g to 1.6 g per diaper, were put into diapers, under the non-woven of the diaper and on top of the pulp. Each diaper also contains 1 g of lipolase 100 T (Novo S Nordisk). For each measurement the pH of the diaper was measured on the non-woven at six different places with a contact electrode. The averaged results are shown in table 4.

TABLE 4

| Amount of g | glycolide added mmol | Starting pH | pH After 1 hour | pH After 2 hours | pH After 5 hours |
|---|---|---|---|---|---|
| 0.2 | 1.7 | 6.0 | 5.1 | 5.0 | 5.0 |
| 0.4 | 3.4 | 5.9 | 5.1 | 4.9 | 4.9 |
| 0.8 | 6.9 | 5.9 | 4.4 | 4.9 | 4.8 |
| 1.6 | 13.8 | 5.9 | 4.8 | 4.6 | 4.6 |

The invention claimed is:

1. Superabsorbent material with odor control containing a non-acidic compound selected from acid anhydrides, cyclic lactides, butyrolactone, valerolactone, glucuronolactone and starch acetate, in which said non-acidic compound is present in an amount of 1-20 wt. % with respect to the weight of the superabsorbent material;
in which the non-acidic compound is a cyclic lactide.

2. Superabsorbent material according to claim 1, in which the non-acidic compound is glycolide.

3. Superabsorbent material according to claim 2, wherein the superabsorbent material is a superabsorbent polymer.

4. Superabsorbent material according to claim 1, in which the non-acidic compound is homogeneously divided in the superabsorbent material.

5. Superabsorbent material according to claim 1, wherein the superabsorbent material is a superabsorbent polymer.

6. Hygiene product with odor control comprising a superabsorbent material containing a non-acidic compound selected from acid anhydrides, cyclic lactides and lactones, in which said non-acidic compound is present in an amount of 1-20 wt. % with respect to the weight of the superabsorbent material;
in which the non-acidic compound is selected from cyclic lactides and lactones of γ- or δ-hydroxy acids,
wherein the hygiene product is a diaper, incontinence pad or sanitary napkin.

7. Hygiene product according to claim 6, wherein the hygiene product is a diaper.

8. Hygiene product according to claim 6, in which the non-acidic compound is a cyclic lactide.

9. Hygiene product according to claim 8, wherein the superabsorbent material is a superabsorbent polymer.

10. Hygiene product according to claim 6, wherein the superabsorbent material is a superabsorbent polymer.

* * * * *